US008870963B2

(12) United States Patent
Gonzalez-Hernandez

(10) Patent No.: US 8,870,963 B2
(45) Date of Patent: Oct. 28, 2014

(54) SYSTEM AND METHOD FOR FRACTURE REPLACEMENT OF COMMINUTED BONE FRACTURES OR PORTIONS THEREOF ADJACENT BONE JOINTS

(75) Inventor: Eduardo Gonzalez-Hernandez, Coconut Grove, FL (US)

(73) Assignee: Toby Orthopaedics, Inc., Miami, FL (US)

( * ) Notice: Subject to any disclaimer, the term of this patent is extended or adjusted under 35 U.S.C. 154(b) by 0 days.

(21) Appl. No.: 13/282,810

(22) Filed: Oct. 27, 2011

(65) Prior Publication Data

US 2012/0109322 A1 May 3, 2012

Related U.S. Application Data

(60) Provisional application No. 61/407,072, filed on Oct. 27, 2010.

(51) Int. Cl.
*A61F 2/40* (2006.01)
*A61B 17/80* (2006.01)
*A61F 2/38* (2006.01)
*A61F 2/30* (2006.01)

(52) U.S. Cl.
CPC .......... *A61B 17/8061* (2013.01); *A61F 2/3859* (2013.01); *A61F 2/4014* (2013.01); *A61F 2002/30578* (2013.01); *A61F 2002/30616* (2013.01); *A61F 2/4003* (2013.01); *A61B 17/80* (2013.01); *A61F 2002/30433* (2013.01)
USPC ...................................... 623/19.14

(58) Field of Classification Search
CPC ....... A61F 2/40; A61F 2/4003; A61F 2/4014; A61F 2002/30433; A61B 17/8061
USPC .................... 623/19.13–19.14, 23.11–23.14
See application file for complete search history.

(56) References Cited

U.S. PATENT DOCUMENTS

| 1,950,799 | A | | 3/1934 | Jones |
| 2,500,370 | A | | 3/1950 | McKibbin |
| 2,555,291 | A | | 5/1951 | Poupitch |
| 2,682,265 | A | * | 6/1954 | Collison ................. 623/23.11 |
| 2,875,663 | A | | 3/1959 | Wieber |
| 3,489,143 | A | | 1/1970 | Halloran |
| 3,552,389 | A | | 1/1971 | Allgower et al. |

(Continued)

FOREIGN PATENT DOCUMENTS

| DE | 86 28 766 U1 | 12/1986 |
| DE | 89 07 443 U1 | 9/1989 |

(Continued)

OTHER PUBLICATIONS

Postak, Paul D.; "Biomechanical Properties of Fixed-Angle Volar Distal Radius Plates Under Dynamic Loading;" 2007; 6 pages.

(Continued)

*Primary Examiner* — Bruce E Snow
(74) *Attorney, Agent, or Firm* — Martin & Ferraro, LLP

(57) ABSTRACT

The system and method serves in facilitating replacement of comminuted bone fractures or portions thereof adjacent bone joints. The system and method employs a prosthesis to replace at least a portion of the comminuted bone fractures. The prosthesis serves in reproducing the articular surface of the portion or portions of the comminuted bone fractures that are replaced. In doing so, the prosthesis serves in restoring joint viability and corresponding articulation thereof.

12 Claims, 2 Drawing Sheets

(56) References Cited

U.S. PATENT DOCUMENTS

| | | | |
|---|---|---|---|
| 3,579,831 | A | 5/1971 | Stevens et al. |
| 3,716,050 | A | 2/1973 | Johnston |
| 3,791,380 | A | 2/1974 | Dawidowski |
| 3,900,025 | A | 8/1975 | Barnes, Jr. |
| 4,263,904 | A | 4/1981 | Judet |
| 4,535,768 | A | 8/1985 | Hourahane et al. |
| 4,683,878 | A | 8/1987 | Carter |
| 4,733,654 | A | 3/1988 | Marino |
| 4,776,330 | A | 10/1988 | Chapman et al. |
| 4,790,302 | A | 12/1988 | Colwill et al. |
| 4,794,919 | A | 1/1989 | Nilsson |
| 4,838,264 | A | 6/1989 | Bremer et al. |
| 4,858,602 | A | 8/1989 | Seidel et al. |
| 4,870,957 | A | 10/1989 | Goble et al. |
| 5,003,969 | A | 4/1991 | Azer et al. |
| 5,015,248 | A | 5/1991 | Burstein et al. |
| 5,041,113 | A | 8/1991 | Biedermann et al. |
| 5,041,114 | A | 8/1991 | Chapman et al. |
| 5,180,383 | A | 1/1993 | Haydon |
| 5,190,544 | A | 3/1993 | Chapman et al. |
| 5,324,291 | A | 6/1994 | Ries et al. |
| 5,356,410 | A | 10/1994 | Pennig |
| 5,364,399 | A | 11/1994 | Lowery et al. |
| 5,423,860 | A | 6/1995 | Lizardi et al. |
| 5,437,667 | A | 8/1995 | Papierski et al. |
| 5,443,516 | A | 8/1995 | Albrektsson et al. |
| 5,458,654 | A | 10/1995 | Tepic |
| 5,462,547 | A | 10/1995 | Weigum |
| 5,472,444 | A | 12/1995 | Huebner et al. |
| 5,505,734 | A | 4/1996 | Caniggia et al. |
| 5,578,035 | A | 11/1996 | Lin |
| 5,584,835 | A | 12/1996 | Greenfield |
| 5,586,985 | A | 12/1996 | Putnam et al. |
| 5,601,553 | A | 2/1997 | Trebing et al. |
| 5,620,449 | A | 4/1997 | Faccioli et al. |
| 5,658,287 | A | 8/1997 | Hofmann et al. |
| 5,665,088 | A | 9/1997 | Gil et al. |
| 5,674,222 | A | 10/1997 | Berger et al. |
| 5,676,667 | A | 10/1997 | Hausman |
| 5,681,311 | A | 10/1997 | Foley et al. |
| 5,709,686 | A | 1/1998 | Talos et al. |
| 5,749,872 | A | 5/1998 | Kyle et al. |
| 5,766,174 | A | 6/1998 | Perry |
| 5,776,194 | A | 7/1998 | Mikol et al. |
| 5,779,704 | A | 7/1998 | Kim |
| 5,785,712 | A | 7/1998 | Runciman et al. |
| 5,840,078 | A | 11/1998 | Yerys |
| 5,868,749 | A | 2/1999 | Reed |
| 5,931,839 | A | 8/1999 | Medoff |
| 5,976,139 | A | 11/1999 | Bramlet |
| 5,980,575 | A * | 11/1999 | Albrektsson et al. ...... 623/23.11 |
| 6,030,389 | A | 2/2000 | Wagner et al. |
| 6,096,040 | A | 8/2000 | Esser |
| 6,149,653 | A | 11/2000 | Deslauriers |
| 6,152,927 | A | 11/2000 | Farris et al. |
| 6,200,330 | B1 | 3/2001 | Benderev et al. |
| 6,206,881 | B1 | 3/2001 | Frigg et al. |
| D443,060 | S | 5/2001 | Benirschke et al. |
| 6,270,499 | B1 | 8/2001 | Leu et al. |
| D449,692 | S | 10/2001 | Michelson |
| 6,302,887 | B1 | 10/2001 | Spranza et al. |
| 6,331,179 | B1 | 12/2001 | Freid et al. |
| 6,348,052 | B1 | 2/2002 | Sammarco |
| 6,358,250 | B1 | 3/2002 | Orbay |
| 6,364,881 | B1 | 4/2002 | Apgar et al. |
| 6,364,882 | B1 | 4/2002 | Orbay |
| 6,379,359 | B1 | 4/2002 | Dahners |
| 6,398,783 | B1 | 6/2002 | Michelson |
| 6,406,478 | B1 | 6/2002 | Kuo |
| 6,409,768 | B1 | 6/2002 | Tepic et al. |
| 6,413,259 | B1 | 7/2002 | Lyons et al. |
| 6,440,135 | B2 | 8/2002 | Orbay et al. |
| 6,468,278 | B1 | 10/2002 | Muckter |
| 6,572,620 | B1 | 6/2003 | Schon et al. |
| 6,620,195 | B2 | 9/2003 | Goble et al. |
| 6,623,486 | B1 | 9/2003 | Weaver et al. |
| 6,663,669 | B1 | 12/2003 | Reiley |
| 6,669,701 | B2 | 12/2003 | Steiner et al. |
| 6,695,844 | B2 | 2/2004 | Bramlet et al. |
| 6,706,046 | B2 | 3/2004 | Orbay et al. |
| 6,712,820 | B2 | 3/2004 | Orbay |
| 6,719,759 | B2 | 4/2004 | Wagner et al. |
| 6,730,090 | B2 | 5/2004 | Orbay et al. |
| 6,776,781 | B1 | 8/2004 | Uwaydah |
| 6,863,671 | B1 | 3/2005 | Strobel et al. |
| 6,866,665 | B2 | 3/2005 | Orbay |
| 6,916,323 | B2 | 7/2005 | Kitchens |
| 6,945,973 | B2 | 9/2005 | Bray |
| 7,001,388 | B2 | 2/2006 | Orbay et al. |
| 7,063,701 | B2 | 6/2006 | Michelson |
| 7,128,744 | B2 | 10/2006 | Weaver et al. |
| D536,453 | S | 2/2007 | Young et al. |
| 7,220,246 | B2 | 5/2007 | Raulerson |
| 7,229,445 | B2 | 6/2007 | Hayeck et al. |
| 7,235,079 | B2 | 6/2007 | Jensen et al. |
| 7,354,441 | B2 | 4/2008 | Frigg |
| 7,500,983 | B1 | 3/2009 | Kaiser et al. |
| 7,563,263 | B2 | 7/2009 | Orbay et al. |
| 7,582,107 | B2 | 9/2009 | Trail et al. |
| 7,591,823 | B2 | 9/2009 | Tipirneni |
| 7,604,657 | B2 | 10/2009 | Orbay et al. |
| 7,637,908 | B1 | 12/2009 | Gonzalez-Hernandez |
| 7,651,517 | B2 | 1/2010 | Konieczynski et al. |
| 7,655,029 | B2 | 2/2010 | Niederberger et al. |
| 7,695,472 | B2 | 4/2010 | Young |
| 7,722,653 | B2 | 5/2010 | Young et al. |
| 7,740,648 | B2 | 6/2010 | Young et al. |
| 7,744,638 | B2 | 6/2010 | Orbay |
| 7,776,076 | B2 | 8/2010 | Grady, Jr. et al. |
| 7,780,667 | B2 | 8/2010 | Watanabe et al. |
| 7,780,710 | B2 | 8/2010 | Orbay et al. |
| 7,896,886 | B2 | 3/2011 | Orbay et al. |
| 7,909,859 | B2 | 3/2011 | Mosca et al. |
| 7,914,532 | B2 | 3/2011 | Shaver et al. |
| 7,927,341 | B2 | 4/2011 | Orbay et al. |
| 7,938,850 | B2 | 5/2011 | Orbay et al. |
| 7,951,176 | B2 | 5/2011 | Grady et al. |
| 7,951,178 | B2 | 5/2011 | Jensen |
| 7,955,364 | B2 | 6/2011 | Ziolo et al. |
| D643,121 | S | 8/2011 | Milford et al. |
| D646,785 | S | 10/2011 | Milford |
| 8,062,367 | B2 | 11/2011 | Kirschman |
| 8,100,953 | B2 | 1/2012 | White et al. |
| 8,182,485 | B1 | 5/2012 | Gonzalez-Hernandez |
| 8,523,902 | B2 | 9/2013 | Heaven et al. |
| 8,574,234 | B2 | 11/2013 | Gonzalez-Hernandez |
| 8,597,363 | B2 | 12/2013 | Liverneaux et al. |
| 8,728,126 | B2 | 5/2014 | Steffen |
| 8,764,808 | B2 | 7/2014 | Gonzalez-Hernandez |
| 2003/0135212 | A1 | 7/2003 | Chow |
| 2003/0135216 | A1 | 7/2003 | Sevrain |
| 2003/0208210 | A1 | 11/2003 | Dreyfuss et al. |
| 2004/0097939 | A1 | 5/2004 | Bonutti |
| 2004/0193278 | A1 | 9/2004 | Maroney et al. |
| 2004/0210220 | A1 | 10/2004 | Tornier |
| 2005/0004574 | A1 | 1/2005 | Muckter |
| 2005/0015089 | A1 | 1/2005 | Young et al. |
| 2005/0021033 | A1 | 1/2005 | Zeiler et al. |
| 2005/0038513 | A1 | 2/2005 | Michelson |
| 2005/0085819 | A1 | 4/2005 | Ellis et al. |
| 2005/0240187 | A1 | 10/2005 | Huebner et al. |
| 2005/0267476 | A1 | 12/2005 | Chervitz et al. |
| 2005/0288681 | A1 | 12/2005 | Klotz et al. |
| 2006/0015072 | A1 | 1/2006 | Raulerson |
| 2006/0015101 | A1 | 1/2006 | Warburton et al. |
| 2006/0161156 | A1 | 7/2006 | Orbay |
| 2006/0217722 | A1 | 9/2006 | Dutoit et al. |
| 2006/0235400 | A1 | 10/2006 | Schneider |
| 2006/0241617 | A1 | 10/2006 | Holloway et al. |
| 2006/0264947 | A1 | 11/2006 | Orbay et al. |
| 2006/0264956 | A1 | 11/2006 | Orbay et al. |
| 2006/0271105 | A1 | 11/2006 | Foerster et al. |
| 2007/0005074 | A1 | 1/2007 | Chudik |
| 2007/0016205 | A1 | 1/2007 | Beutter et al. |

(56) References Cited

U.S. PATENT DOCUMENTS

| | | |
|---|---|---|
| 2007/0083207 A1 | 4/2007 | Ziolo et al. |
| 2007/0123880 A1 | 5/2007 | Medoff |
| 2007/0123885 A1 | 5/2007 | Kirschman |
| 2007/0162015 A1 | 7/2007 | Winquist et al. |
| 2007/0167953 A1 | 7/2007 | Prien et al. |
| 2007/0233114 A1 | 10/2007 | Bouman |
| 2007/0233115 A1 | 10/2007 | Sixto et al. |
| 2008/0015593 A1 | 1/2008 | Pfefferle et al. |
| 2008/0045960 A1 | 2/2008 | Bruecker et al. |
| 2008/0132955 A1 | 6/2008 | Frigg |
| 2008/0140130 A1 | 6/2008 | Chan et al. |
| 2008/0154311 A1 | 6/2008 | Staeubli |
| 2008/0161853 A1 | 7/2008 | Arnold et al. |
| 2008/0161860 A1 | 7/2008 | Ahrens et al. |
| 2008/0161863 A1 | 7/2008 | Arnold et al. |
| 2008/0221577 A1 | 9/2008 | Elghazaly |
| 2008/0234749 A1 | 9/2008 | Forstein |
| 2008/0234752 A1 | 9/2008 | Dahners |
| 2008/0249572 A1 | 10/2008 | Tandon |
| 2009/0012571 A1 | 1/2009 | Perrow et al. |
| 2009/0024173 A1 | 1/2009 | Reis, Jr. |
| 2009/0048681 A1* | 2/2009 | Vlachos ............... 623/23.12 |
| 2009/0076554 A1 | 3/2009 | Huebner et al. |
| 2009/0105838 A1* | 4/2009 | Russo et al. ............ 623/19.14 |
| 2009/0171399 A1 | 7/2009 | White et al. |
| 2009/0192550 A1 | 7/2009 | Leung et al. |
| 2009/0216270 A1 | 8/2009 | Humphrey |
| 2009/0228010 A1 | 9/2009 | Gonzalez-Hernandez et al. |
| 2009/0254089 A1 | 10/2009 | Tipirneni et al. |
| 2009/0254189 A1 | 10/2009 | Scheker |
| 2009/0264936 A1 | 10/2009 | Gonzalez-Hernandez |
| 2009/0275987 A1 | 11/2009 | Graham et al. |
| 2009/0275991 A1 | 11/2009 | Medoff |
| 2009/0281578 A1 | 11/2009 | Spencer |
| 2009/0299369 A1 | 12/2009 | Orbay et al. |
| 2009/0306711 A1 | 12/2009 | Stone et al. |
| 2009/0312760 A1 | 12/2009 | Forstein et al. |
| 2009/0312802 A1 | 12/2009 | Dasilva |
| 2009/0326591 A1 | 12/2009 | Spencer, Jr. |
| 2010/0030276 A1 | 2/2010 | Huebner et al. |
| 2010/0057086 A1 | 3/2010 | Price et al. |
| 2010/0145339 A1 | 6/2010 | Steffen |
| 2010/0198258 A1 | 8/2010 | Heaven et al. |
| 2010/0217393 A1 | 8/2010 | Theofilos |
| 2010/0262194 A1 | 10/2010 | Wagner et al. |
| 2010/0274245 A1 | 10/2010 | Gonzalez-Hernandez |
| 2010/0324602 A1 | 12/2010 | Huebner et al. |
| 2010/0331844 A1 | 12/2010 | Ellis et al. |
| 2011/0152943 A1 | 6/2011 | Gonzalez-Hernandez |
| 2012/0083848 A1 | 4/2012 | Gonzalez-Hernandez |
| 2012/0109322 A1 | 5/2012 | Gonzalez-Hernandez |
| 2012/0197305 A1 | 8/2012 | Gonzalez-Hernandez |
| 2012/0197308 A1 | 8/2012 | Gonzalez-Hernandez |
| 2012/0226321 A1 | 9/2012 | Gonzalez-Hernandez |
| 2012/0226322 A1 | 9/2012 | Gonzalez-Hernandez |
| 2012/0226323 A1 | 9/2012 | Gonzalez-Hernandez |
| 2013/0096629 A1 | 4/2013 | Rollinghoff et al. |
| 2013/0116734 A1 | 5/2013 | Gonzalez-Hernandez |
| 2013/0289627 A1 | 10/2013 | Gonzalez-Hernandez |
| 2014/0121709 A1 | 5/2014 | Gonzalez-Hernandez |
| 2014/0121779 A1 | 5/2014 | Gonzalez-Hernandez |
| 2014/0172020 A1 | 6/2014 | Gonzalez-Hernandez |

FOREIGN PATENT DOCUMENTS

| | | |
|---|---|---|
| DE | 43 43 117 A1 | 6/1995 |
| DE | 198 57 279 A1 | 6/2000 |
| DE | 299 07 161 U1 | 8/2000 |
| EP | 0 551 588 A1 | 11/1992 |
| EP | 1 132 052 A2 | 9/2001 |
| EP | 1 468 655 A2 | 10/2004 |
| FR | 2 606 268 A1 | 5/1988 |
| FR | 2 680 673 A1 | 3/1993 |
| JP | 4-138152 A | 5/1992 |
| WO | WO 99/38448 A1 | 8/1999 |
| WO | WO 2005/037117 A1 | 4/2005 |
| WO | WO 2008/007194 A2 | 1/2008 |
| WO | WO 2008/007196 A2 | 1/2008 |
| WO | WO 2012/003884 | 1/2012 |

OTHER PUBLICATIONS

Synthes, "Large Fragment LCP Instrument and Implant Set" technique guide; 2003; 31 pages.
Synthes, "Locking Compression Plate (LCP) System. Locking screw technology and conventional plating in one system;" 2003; 6 pages.
Synthes; Modular Mini Fragment LCP System (brochure); 2007; 12 pages.
Synthes; Small Fragment Locking Compression Plate (LCP) System (brochure); 2002; 43 pages.
Zimmer, Inc. "Zimmer® Universal Locking System," brochure (2006), 4 pages.
U.S. Appl. No. 10/993,723, filed Nov. 2004, Gonzalez-Hernandez.
U.S. Appl. No. 11/050,304, filed Feb. 2005, Gonzalez-Hernandez.
U.S. Appl. No. 11/079,350, filed Mar. 2005, Gonzalez-Hernandez.
U.S. Appl. No. 11/366,676, filed Mar. 2006, Gonzalez-Hernandez.
U.S. Appl. No. 11/493,122, filed Jul. 2006, Gonzalez-Hernandez.
U.S. Appl. No. 11/526,331, filed Sep. 2006, Gonzalez-Hernandez.
U.S. Appl. No. 11/707,775, filed Feb. 2007, Gonzalez-Hernandez.
U.S. Appl. No. 13/253,564, filed Oct. 2011, Gonzalez-Hernandez.
U.S. Appl. No. 13/411,069, filed Mar. 2012, Gonzalez-Hernandez.
U.S. Appl. No. 13/411,100, filed Mar. 2012, Gonzalez-Hernandez.
U.S. Appl. No. 13/412,039, filed Mar. 2012, Gonzalez-Hernandez.
ACUMED; ACU-LOC Wrist Plating System; Jul. 2009; 20 pages.
ACUMED; The Mayo Clinic Congruent Elbow Plates (catalog); 2003; 19 pages.
ACUMED; The Mayo Clinic Congruent Elbow Plates (catalog); Apr. 2006; 20 pages.
Christie, J., C.R. Howie and P.C. Armour, Fixation of displaced subcapital femoral fractures. Compression screw fixation versus double divergent pins, *J Bone Joint Surg* [Br]1988; 70-B; 199-201.
Cross, W.M. et al., "Achieving stable fixation: biomechanical designs for fracture healing," AAOS Now (2008) 3 pages.
Guha, AR, et al.; "A New Technique of Fixation of Radial Head Fractures Using a Modified Tubular Plate," Journal of Postgraduate Medicine; Jul. 2004; vol. 50, Issue 2; pp. 113-114; Accessed Aug. 6, 2008 at: http://www.jpgmonline.com/article.asp?issn=0022-3859; year=2004;volume=50;issue=2;spage=113;epage=114;aulast=Guha.
Hand Innovations, LLC; DVR Anatomic, Volar Plating System; 2007; 4 pages.
Hussain M., R.N. Natarajan, A.H. Fayyazi, B.R. Braaksrna, G,B, Andersson and H.S. An, *Screw angulation affects bone-screw stresses and bone graft load sharing in an anterior cervical corbectomy fusion with a rigid screw-plate construct: a finite element model study*; Spine Journal, vol. 9, Issue 12; Dec. 2009; pp. 1016-1023 (published online Oct. 12, 2009).
Lakatos, R. et al.; "General principles of internal fixation"; eMedicine; Aug. 2006; 51 pages.
"MIS Technique," published by Zimmer®, 1 page (undated).
Robert, III, K.Q., R. Chandler, R,V, Barratta, K.A. Thomas and M.B. Harris, The effect of divergent screw placement on the initial strength of plate-to-bone fixation. *J Trauma.* Dec. 2003;55(6):1139-44.
Synthes; 3.5 mm LCP Periarticular Proximal Humerus Plate; Apr. 2010; 22 pages.
Synthes; Locking Compression Plate (LCP) System (brochure); 2003; 6 pages.
Synthes; Locking Compression Plate (LCP) System (brochure); Jan. 2007; 6 pages.
Written Opinion of the International Searching Authority; International Application No. PCT/US2009/036211; Sep. 23, 2010; 8 pages.
"Zimmer® Universal Locking System;" The Journal of Bone and Joint Surgery, vol. 89, No. 7, Jul. 2007, 1 page.
Zimmer; Inc.; "Zimmer Universal Locking System;" brochure; 2009, 2 pages.
Zimmer; Inc. "Zimmer Holdings to Launch Innovative Locking Plate System at Orthopaedic Trauma Association Meeting," Sep. 14, 2006; 3 pages.

(56) References Cited

OTHER PUBLICATIONS

Zimmer; Inc.; "Zimmer Small Fragment Universal Locking System;" Surgical Technique; 2010; 16 pages.
Zimmer; Zimmer Perlarticular Plating System-Low-Profile Fixation (catalog); 2003; 8 pages.
U.S. Appl. No. 13/663,129, filed Oct. 2012, Gonzalez-Hernandez.
U.S. Appl. No. 13/663,209, filed Oct. 2012, Gonzalez-Hernandez.
U.S. Appl. No. 13/840,194, filed Mar. 2013, Gonzalez-Hernandez.
U.S. Appl. No. 14/189,681, filed Feb. 2014, Gonzalez-Hernandez.
U.S. Appl. No. 14/213,310, filed Mar. 2014, Gonzalez-Hernandez.

* cited by examiner

SYSTEM AND METHOD FOR FRACTURE REPLACEMENT OF COMMINUTED BONE FRACTURES OR PORTIONS THEREOF ADJACENT BONE JOINTS

RELATED APPLICATIONS

This non-provisional application claims the benefit of U.S. Provisional Application No. 611/407,072, filed Oct. 27, 2010, entitled "Proximal Humerus Hybrid Prosthesis Plate and Method of Use Associated Therewith"; the entire contents of which is hereby incorporated by reference herein.

BACKGROUND

1. Field of the Invention

The present invention is generally related to a medical device and method for use thereof for facilitating replacement of comminuted bone fractures. In particular, the present invention is related to a system and method for use thereof to aid in the replacement of comminuted bone fractures adjacent bone joints to restore joint viability. More specifically, the present invention relates to a system and method for use thereof for replacing comminuted bone fractures adjacent joints by providing a prosthesis to replace the fractured bone to facilitate restoration of movement associated with the bone joint.

2. Description of the Prior Art

Comminuted bone fractures adjacent joints oftentimes result in significant fragmentation of the bone. In fact, these types of bone fractures can often result in portions of the bone being severely fragmented. That is, the number of fragments created by these types of bone factures pose difficulties in repairing the bone. Bone plates have oftentimes been used to aid repair of the comminuted bone fractures. However, even with use of bone plates, the comminuted bone fractures may not be adequately reconstructed. For example, if severely fragmented, the proximal and distal end portions of a humerus may not be reconstructible. As such, there is a need for a prosthesis affording replacement of the comminuted bone fractures or portions thereof to restore joint viability. The prosthesis can be used when the comminuted bone fractures need substantial support to aid repair or are irretrievably fragmented. Such a prosthesis, for example, can be configured to repair the proximal and distal ends of the humerus.

SUMMARY OF THE INVENTION

The present invention in one embodiment contemplates a method for replacing at least a portion of a comminuted humeral head, the method including the following acts. A prosthesis is provided that has an exterior portion having an exterior surface, and an interior portion having at least one aperture formed therein, the exterior surface approximating the surface of the at least a portion of the comminuted humeral head in size and shape, and the at least one aperture of the prosthesis being configured to receive at least one fastener therein. A bone plate is provided that has at least one opening formed therein, the at least one aperture of the bone plate being configured to receive the at least one fastener therethrough. At least a portion of the comminuted humeral head is removed. The bone plate is attached to at least a portion of a humerus. The at least one aperture of the prosthesis is aligned with the at least one opening of the bone plate. The at least one fastener is inserted through the at least one opening and into the at least one aperture. The prosthesis and the bone plate are securely attached to one another across the humerus using the fastener.

In another preferred embodiment, the present invention contemplates a system for replacement of at least a portion of a comminuted humeral head. The system includes a prosthesis, a bone plate, and at least one fastener. The prosthesis has an exterior portion having an exterior surface and an interior portion having at least one aperture formed therein, the exterior surface being sized and shaped to approximate the surface of the at least a portion of the comminuted humeral head, and the at least one aperture of the prosthesis configured to receive at least one fastener therein. The bone plate including at least one opening formed therein, the at least one opening of the bone plate being configured to receive the at least one fastener therethrough. The at least one fastener having a first end for insertion through the at least one opening and into the at least one aperture, the at least one fastener being configured to secure attachment of the prosthesis and the bone plate to one another across a portion of a humerus.

In yet another preferred embodiment, the present invention contemplates a method for replacing at least a portion of a fractured capitellum and/or a fractured trochlea, the method including the following acts. An apparatus is provided that has a prosthesis portion and a plate portion, the prosthesis portion having an exterior surface, and the plate portion including a first leg portion extending outwardly from the prosthesis portion and a second leg portion extending outwardly from the prosthesis portion. At least a portion of the fractured capitellum and/or the fractured trochlea is removed. The prosthesis portion is sized and shaped according to the portion of the fractured capitellum and/or the fractured trochlea removed, the prosthesis portion having an exterior surface approximating the exterior surface of the removed portion of the fractured capitellum and/or the fractured trochlea. The prosthesis portion is positioned relative to the humerus. The first leg portion is attached to the lateral column of the humerus and the second leg portion is attached to the medial column of the humerus.

It is understood that both the foregoing general description and the following detailed description are exemplary and exemplary only, and are not restrictive of the invention as claimed.

BRIEF DESCRIPTION OF THE DRAWINGS

The accompanying drawings, which are incorporated in and constitute a part of the specification, illustrate preferred embodiments of the invention. Together with the description, they serve to explain the objects, advantages and principles of the invention. In the drawings.

DETAILED DESCRIPTION OF THE PREFERRED EMBODIMENT

The systems for fracture replacement of comminuted bone fractures or portions thereof and the method for use of the system are depicted in the accompanying drawings. The systems of the present invention provide a prosthesis affording replacement of the comminuted bone fractures or portions thereof. While the below-described systems are used in association with the proximal and distal end portions of a humerus, the present invention is not limited thereto. That is, the system and method of the present invention can be configured for use elsewhere in the human body.

Figure 1:
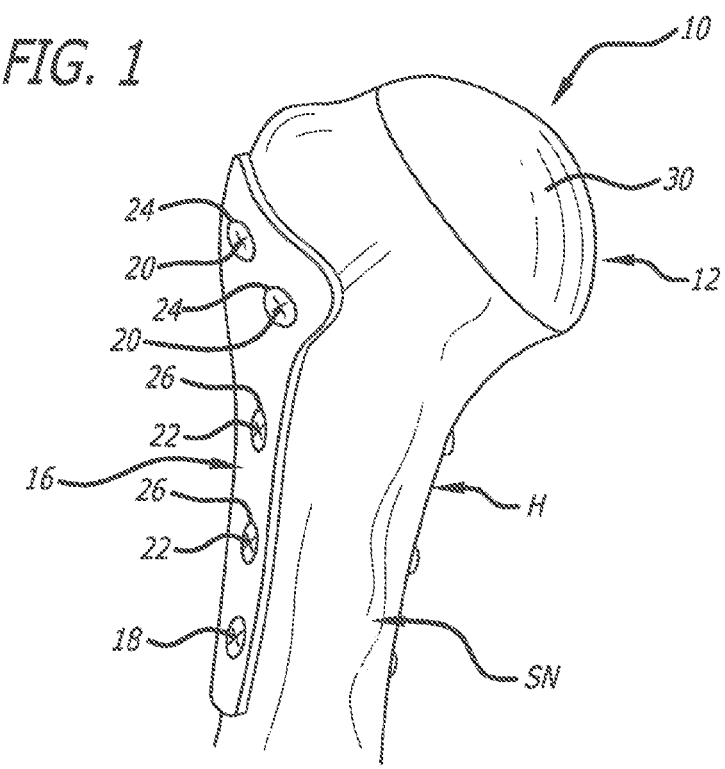
FIG. 1 is a perspective view of a first embodiment of a system for fracture repair and/or replacement for use with and depicted as attached to a proximal portion of a humerus.
Figure 2:
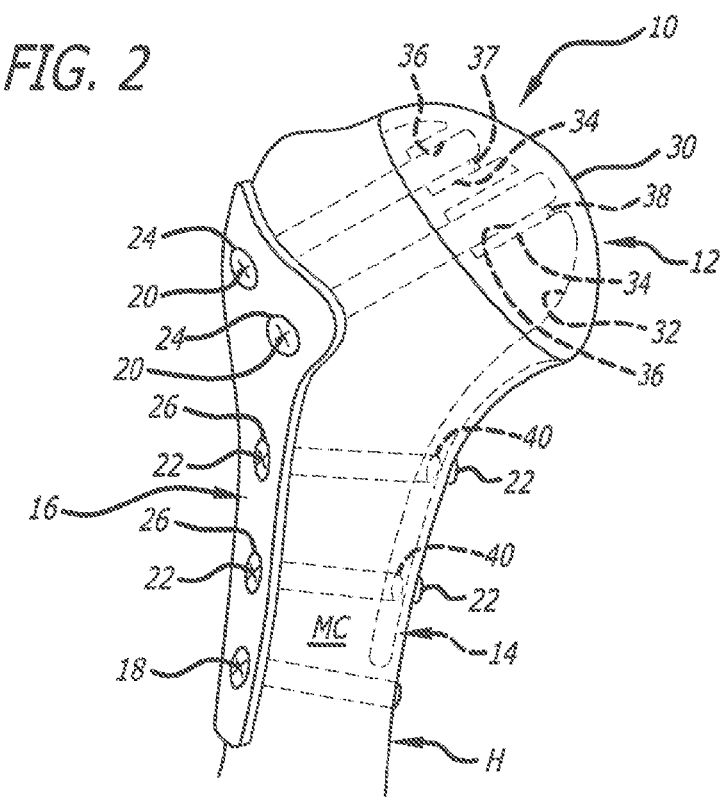
FIG. 2 is the perspective view of FIG. 1 showing a humeral head prosthesis, an extension portion, and fasteners of the first embodiment of the system in phantom with respect to the humerus.

A first illustrative embodiment of the system is generally indicated by the numeral in FIGS. 1 and 2, and a second illustrative embodiment of the system is generally indicated by the numeral 100 in FIGS. 3-6A. First system 10 is used in replacing a fractured humeral head or portions thereof at the proximal end of the humerus and second system 100 is used in replacing a fractured capitellum and/or a fractured trochlea or portions thereof at the distal end of the humerus. In doing so, first and second systems 10 and 100 serve to repair the proximal and distal ends, respectively, of the humerus, and serve in restoring joint viability. The components of each of systems 10 and 100 are constructed of metal or other artificial material suitable for human implantation.

First system 10 is provided to facilitate replacement of a humeral head or portions thereof (not shown) at the proximal end of a humerus H (FIGS. 1 and 2) that have been irretrievably fragmented. Furthermore, while first system 10 is depicted replacing the humeral head or portion thereof, first system 10, for example, could be configured for replacing portions of a distal ulna. First system 10 includes a head portion 12 (or prosthetic portion), an optional extension portion 14 (of the medial calcar), and a bone plate 16. Head portion 12 serves as prosthesis for replacement of the humeral head or portions thereof, and bone plate 16 is configured to provided a rigid structure for attaching head portion 12 and extension portion 14 thereto. Extension portion 14 provides additional structural integrity, but, depending on the needs of the patient, may not be necessary.

Bone plate 16 is attached to surgical neck SN of humerus H. Bone plate 16 is configured to receive one or more bone screws 18 therethrough for attachment to surgical neck SN. Bone screws 18 are exclusively used for attachment of bone plate 16 to surgical neck SN.

Bone plate 16 also is configured to receive fasteners (such as bolts, posts, and/or screws) 20 and 22 for engagement with head portion 12 and extension portion 14, respectively. If fasteners 20 and 22 are bolts and/or screws, then fasteners 20 and 22 could threadably engage head portion 12 and extension portion 14, respectively, to facilitate attachment. Furthermore, if fasteners 20 and 22 are posts, then fasteners 20 and 22 could be attached to head portion 12 and extension portion 14, respectively, using interference fits therebetween. Thus, whether fasteners 20 and 22 are bolts, posts, and/or screws, the fasteners, and head portion 12 and extension portion 14 would include complementary structures facilitating attachment.

To facilitate engagement of bone plate 16 with head portion 12 and extension portion 14 using fasteners 20 and 22, respectively, bone plate 16 includes openings 24 and 26 therethrough. Openings 24 are provided at or adjacent the upper portion of bone plate 16 for receiving fasteners 20, and openings 26 are provided at or adjacent the middle portion of bone plate 16 for receiving fasteners 22. After insertion thereof through bone plate 16, fasteners 20 and 22 engage head portion 12 and extension portion 14, respectively, to provide for the rigid attachment of humeral head prosthesis to humerus H. In addition to threads (not shown) or structures (not shown) for providing for an interference fit to facilitate engagement with head portion 12 and extension portion 14, fasteners 20 and 22 can include threads (not shown) for engaging complementary threads (not shown) provided in openings 24 and 26 to lock fasteners 20 and 22 to bone plate 16. Moreover, fasteners 20 and 22 could include threads facilitating attachment to portions of humerus H that fasteners 20 and 22 extend through.

Head portion 12 can be sized and shaped according to the portions of the humeral head being replaced. As such, portions of head portion 12 serve in reproducing the articular surface of the proximal humerus that is being replaced using system 10. Thus, if only a portion of the humeral head requires replacement, head portion 12 can be sized and shaped to approximate the size and shape of the portion of the humeral head being replaced. However, if the entirety of the humeral head is being replaced, head portion 12 can be sized and shaped to approximate the size and shape of the entirety of the humeral head. As depicted in FIGS. 1 and 2, head portion 12 is sized and shaped to replace the entirety of the humeral head.

Head portion 12 includes an exterior-facing portion having an exterior surface 30, and an interior-facing portion of having an interior surface 32, columns 34, and apertures 36 for receiving fasteners 20 therein. Apertures 36 can include complementary threads (not shown) or structures (not shown) for providing an interference fit to facilitate engagement with fasteners 20. As depicted in FIGS. 1 and 2, exterior surface 30 is convex and is configured to mimic the shape of the humeral head or portions thereof to reproduce the articular surface of the proximal humerus being replaced. Accordingly, portions of exterior surface 30 can be highly polished or lubricated. Furthermore, as depicted in FIG. 2, interior surface 32 is concave, and columns 34 extend outwardly from interior surface 32.

Columns 34 include apertures 36 for receiving fasteners 20 therein. However, the present invention is not limited to using columns 34. For example, if interior surface 32 is flattened (rather than concave) and an adequate depth of material is provided between exterior surface 30 and interior surface 32, apertures 36 could be formed through interior surface 32 into the material provided between exterior surface 30 and interior surface 32.

Furthermore, relief holes 38 are provided through columns 34 to communicate with apertures 36. Relief holes 38 allow tissues, fluids, and/or air that were present in apertures 36 (prior to insertion of fasteners 20 therein) to be expelled therefrom as fasteners 20 are tightened in position.

While head portion 12 is depicted in FIGS. 1 and 2 as being a single integral component, head portion 12 can be composed of two or more elements that can be integrated with one another during implantation of system 10. For example, head portion 12 could be composed of a base plate (not shown) and a portion (not shown) including exterior surface 30. The base plate would first be attached to bone plate 16 using fasteners 20, and then the portion including exterior surface 30 would be attached to the base plate. The base plate and the portion including exterior surface 30 could include a complementary attachment mechanism shared therebetween to facilitate integration thereof. As such, a standard sized and shaped base plate could be utilized, and only the portion including exterior surface 30 would be sized and shaped according to the portions of the humeral head being replaced.

Extension portion 14, as depicted in FIG. 2, depends downwardly from head portion 12. Extension portion 14 is inserted into medullary cavity MC, and is configured to interface with the bone adjacent medullary cavity MC. Furthermore, using fasteners 22, extension portion 14 can be attached to the medial cortex of humerus H. To that end, extension portion 14 includes apertures 40 for receiving fasteners 22. Like apertures 36 of head portion 12, apertures 40 can also include complementary threads (not shown) or structures (not shown) for providing an interference fit to facilitate engagement with fasteners 22.

Rather than or in addition to using fasteners 20 and 22, integral posts (not shown) formed with bone plate 16 could be used to attach bone plate 16 with head portion 12 and/or extension portion 14. For example, an integral post that extends outwardly from bone plate 16 could be positioned adjacent apertures 24. Furthermore, a portion of the integral post could be received in one of apertures 36, and the integral post and the one of apertures 36 could include complementary structures (not shown) facilitating attachment therebetween.

Moreover, while fasteners 20 and 22 are shown as being inserted through bone plate 16 and into head portion 12 and extension portion 14, respectively, head portion 12, extension portion 14, and bone plate 16 could be configured to provide the opposite arrangement—fasteners 20 and 22 could be inserted through head portion 12 and extension portion 14, respectively, and into bone plate 16. As such, head portion 12, extension portion 14, and bone plate 16 would include complementary configurations to afford such an arrangement. For example, head portion 12 could include an opening (not shown) extending through the exterior-facing portion and the interior-facing portion thereof. Thus, a fastener (similar, if not identical, to fastener 20) could be inserted through such an opening and into a corresponding aperture formed in bone plate 16.

To secure attachment of first system 10 to humerus H using the configuration thereof depicted in FIGS. 1 and 2, the fractured humeral head or portions thereof are removed from adjacent humerus H. Bone plate 16 is initially attached to surgical neck SN using bone screw 18. Thereafter, openings 24 and 26 through bone plate 16 can be used as drill guides for receiving a drill to create alignment holes through humerus H. The alignment holes created by the drill will ultimately afford alignment between holes 24 in bone plate 16 and apertures 36 in head portion 12, and between holes 26 in bone plate 16 and apertures 40 in extension portion 14. Once the alignment holes are created, head portion 12 is positioned with respect to humerus H. Fasteners 20 and 22 are then inserted through openings 24 and 26 into apertures 36 and 49, respectively. Tightening of fasteners 20 and 22 in holes 36 and 40 serve to secure engagement of head portion 12 to humerus 10. As such, head portion 12, extension portion 14, and bone plate 16 and fasteners 20 and 22 extending therebetween provide an effective structural lattice allowing head portion 12 to provide an effective replacement for the humeral head or portions thereof that are severely fractured. Via replacement of the humeral head or portions thereof using first system 10, the viability of the shoulder joint adjacent to head portion 12 can be restored.

As discussed above, second system 100 is provided to facilitate replacement of a fractured capitellum and/or a fractured trochlea or portions thereof (not shown) at the distal end of the humerus. As depicted in FIGS. 3-6A, second system 100 includes a prosthetic portion 102 and a plate portion 104. Prosthetic portion 102 and plate portion 104 are depicted in FIGS. 3-6A as being formed integrally with one another. However, second system 100 is not limited thereto. Prosthetic portion 102 and plate portion 104 can be formed separately from one another and then cooperatively engaged to (or integrated with) one another. For example, prosthetic portion 102 and plate portion 104 could be fastened to one another using a fastener extending through portions thereof during implantation of system 100. Furthermore, while second system 100 is configured to replace the fractured capitellum and/or the fractured trochlea or portions thereof, second system 100 is not limited thereto. For example, second system 100 also could be configured to replace fractured portions of the humerus such as the lateral epicondyle, the olecranon fossa, and/or medial epicondyle.

Prosthetic portion 102 serves as a prosthesis for replacement of the fractured capitellum and/or the fractured trochlea or portions thereof. As such, prosthetic portion 102 could be shaped to replace the entirety of both of the fractured capitellum and the fractured trochlea, or various portions of the fractured capitellum and/or the fractured trochlea. Furthermore, plate portion 104 is configured to provide a rigid structure for attaching prosthetic portion 102 to the humerus.

Figure 3:
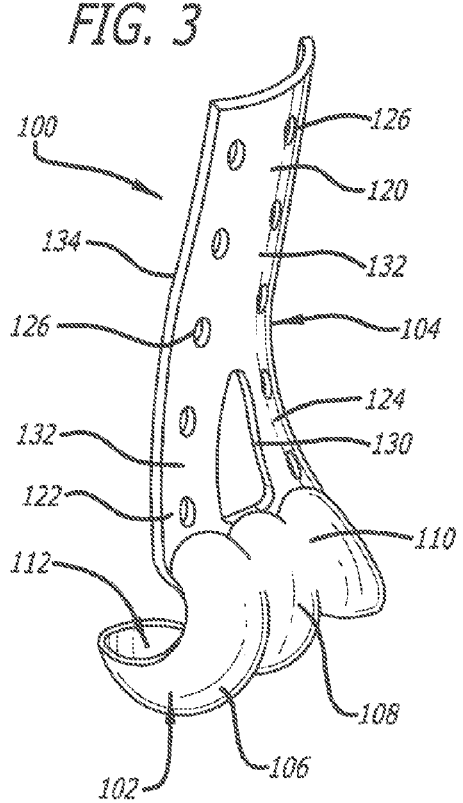
FIG. 3 is a perspective view of a second embodiment of the system for fracture repair and/or replacement for use with a distal portion of the humerus.
Figure 4:
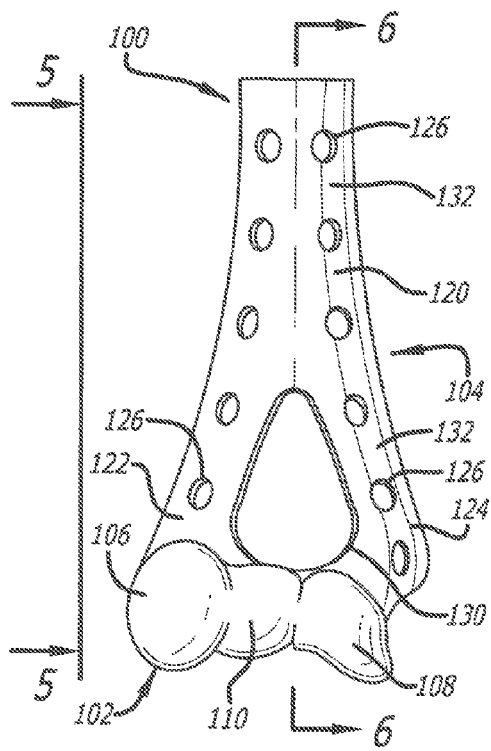
FIG. 4 is a front elevational view of the second embodiment of the system depicted in FIG. 3.
Figure 5:
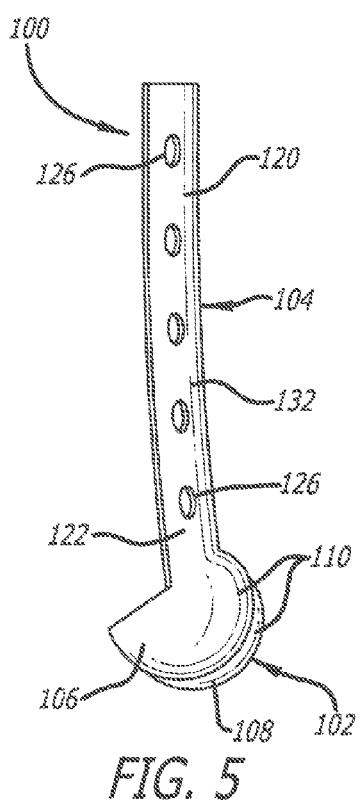
FIG. 5 is a side elevational view of the second embodiment of the system depicted in FIGS. 3 and 4.

As depicted in FIGS. 3-5, prosthetic portion 102 includes a capitellum portion 106 and a trochlea portion 108. As discussed above, the entirety of the fractured capitellum and/or the fractured trochlea or portions thereof can be replaced using prosthetic portion 102. Thus, prosthetic portion 102 includes an exterior surface 110 (extending over capitellum portion 106 and trochlea portion 108) that can be sized and shaped according to the portions of the fractured capitellum and/or the fractured trochlea requiring replacement. As such, portions of prosthetic portion 102 serve in reproducing the articular surface of the distal humerus that is being replaced using system 100. Accordingly, portions of exterior surface 110 can be highly polished or lubricated.

For example, if only the entirety of fractured capitellum requires replacement, then prosthetic portion 102 (and exterior surface 110 thereof) would be sized and shaped to approximate the entirety of the capitellum and could incorporate only capitellum portion 106. Furthermore, if only the entirety of the fractured trochlea requires replacement, prosthetic portion 102 (and exterior surface 110 thereof) would be sized and shaped to approximate the entirety of the trochlea and could incorporate only trochlea portion 108. However, if only selected portions of the fractured capitellum and the fractured trochlea require replacement, then prosthetic portion 102 (and exterior surface 110 thereof) would be sized and shaped to approximate the selected portions by incorporating corresponding portions of capitellum portion 106 and trochlea portion 108.

Figure 6:
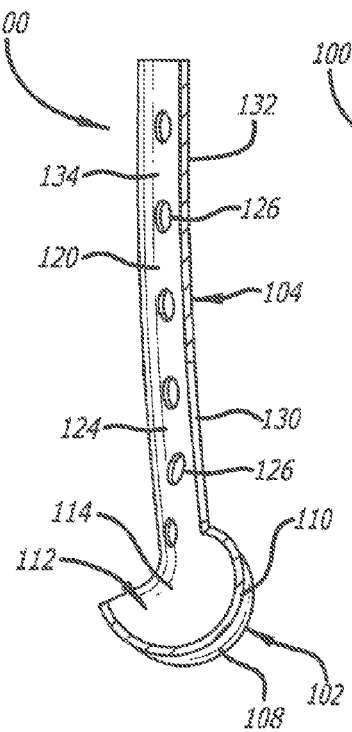
FIG. 6 is a cross-sectional view of the second embodiment of the system depicted in FIGS. 3-5 taken along Line 6-6 of FIG. 4.
Figure 6A:
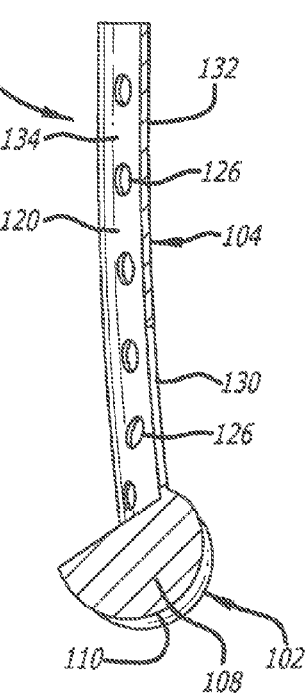
FIG. 6A is a alternative cross section for the second embodiment of the system depicted in FIGS. 3-6.

Furthermore, prosthetic portion 102 can be constructed to be hollow to include a cavity 112. As depicted in FIGS. 3 and 6, cavity 112 is formed behind exterior surface 110, and thus, an interior surface 114 (of cavity 112) is opposite exterior surface 110. Cavity 112 can be filled with bone graft materials, and/or portions of the fractured capitellum and the fractured trochlea that the prosthetic portion 102 is being used to replace. Alternatively, prosthetic portion 102 can be constructed of solid material as depicted in the cross-sectional view of FIG. 6A. As such, prosthetic portion 102 would be formed of solid material approximating the portions of the fractured capitellum and/or the fractured trochlea being replaced.

As depicted in FIGS. 3 and 4, plate portion 104 extends outwardly from prosthetic portion 102, and includes a body portion 120, a first leg portion 122, and a second leg portion 124. First leg portion 122 extends outwardly from capitellum portion 106, and second leg portion 124 extends outwardly from trochlea portion 108. Furthermore, first and second leg portions 122 and 124 extend from prosthetic portion 102 to terminate at body portion 120.

An aperture 130, as depicted in FIGS. 3 and 4 is formed between prosthesis portion 102 and first and second leg portions 122 and 124. Furthermore, plate portion 104 includes a front surface 132 and a rear surface 134 opposite the front surface 132. As discussed below, portions of rear surface 134 (which encompasses body portion 120, first leg portion 122, and second leg portion 124) is engaged to portions of the humerus. As such, rear surface 134 can be at least in part concave (FIG. 6) to facilitate such engagement.

Body portion 120 is attached to the shaft (not shown) of the humerus. Furthermore, first leg portion and second leg portions 122 and 124 are attached to the humerus—first leg portion 120 is attached to the lateral column (not shown) and second leg portion 122 is attached to the medial column (not shown). To that end, body portion 120, first leg portion 122, and second leg portion 124 can include various apertures 126. Apertures 126 can be configured to receive bone screws (not shown) therethrough to attach plate portion 104 to the humerus.

In addition to threads (not shown) for engaging the humerus, the bone screws used to attach the plate portion thereto can include threads (not shown) for engaging complementary threads (not shown) provided in apertures 126 to lock the bone screws to plate portion 104. Furthermore, if necessary, a second plate portion (not shown) can be positioned on the opposite side of the humerus of plate portion 104 to afford another attachment structure for plate portion 104. Thus, additional fasteners (such as bolts and/or screws) could be used to interconnect plate portion 104 and the second plate portion to further enhance the rigidity of the structure attaching prosthetic portion 102 to the humerus.

To secure attachment of the first system 100 to the humerus, the fractured capitellum and/or the fractured trochlea or portions thereof are removed from adjacent the humerus. Thereafter, plate portion 104 is attached to the humerus with or without drilling into the humerus. If holes are drilled in the humerus to receive the bone screws, apertures 126 through plate portion 104 can be used as drill guides for receiving a drill. The bone screws are thereafter inserted through apertures 126 and into the humerus. Using the bone screws to facilitate attachment to the humerus, body portion 120 is attached to the shaft, first leg portion 120 is attached to the lateral column, and second leg portion 122 is attached to the medial column. The attachment of body portion 120, first leg portion 122, and second leg portion 124 to the humerus provides the structural rigidity necessary to allow prosthetic portion 102 to provide an effective replacement for the fractured capitellum and/or the fractured trochlea or portions thereof, Via replacement of the fractured capitellum and/or the fractured trochlea or portions thereof using second system 100, the viability of the elbow joint adjacent to prosthesis portion 102 can be restored.

In summary, systems 10 and 100 for replacement of comminuted bone portions and the method for use thereof provide a prosthesis affording replacement of the comminuted bone fractures or portions thereof. Furthermore, while systems 10 and 100 are used in association with the proximal and distal end portions, respectively, of the humerus, the system and method of the present invention can be configured for use elsewhere in the human body. Other embodiments of the invention will be apparent to those skilled in the art from consideration of the specification and practice of the invention disclosed herein. Accordingly, it is intended that the specification and examples be considered as exemplary only.

What is claimed is:

1. A method for replacing at least a portion of a comminuted humeral head of a humerus, the method comprising:
    utilizing a prosthesis having an exterior portion having an exterior surface, and an interior portion having at least one first aperture and at least one second aperture formed therein, the exterior surface approximating the surface of the at least a portion of the comminuted humeral head in size and shape;
    utilizing a bone plate, said bone plate including an upper portion adapted to attach to the humerus at a position proximate a surgical neck thereof, and an elongated lower portion adapted to attach to a shaft of the humerus, said upper portion including at least one first opening and at least one second opening formed therein, the at least one first opening and the at least one second opening of said upper portion of said bone plate being configured to receive at least one first fastener and at least one second fastener, respectively, therethrough, said elongated lower portion of said bone plate including at least one third opening formed therein, the at least one third opening of said elongated lower portion of said bone plate being configured to receive at least one third fastener therethrough;
    removing at least a portion of the comminuted humeral head;
    aligning the at least one first aperture of said prosthesis with the at least one first opening of said upper portion of said bone plate and aligning the at least one second aperture of said prosthesis with the at least one second opening of said upper portion of said bone plate;
    inserting the at least one first fastener through the at least one first opening in said upper portion of said bone plate and into the at least one first aperture in said prosthesis and inserting the at least one second fastener through the at least one second opening in said upper portion of said bone plate and into the at least one second aperture in said prosthesis; and
    inserting the at least one third fastener through the at least one third opening in the elongated lower portion of said bone plate and into the shaft of the humerus, thereby securing attachment of said prosthesis and said bone plate to one another and to the humerus, using the at least one first, second, and third fasteners.

2. The method of claim 1, wherein the removing further comprises removing portions of the comminuted humeral head that are irretrievably fragmented.

3. The method of claim 1, wherein said bone plate is attached to a side of the humerus opposite from the position of the comminuted humeral head.

4. The method of claim 1, wherein the securing attachment further comprises securing said prosthesis and said bone plate in fixed position relative to the humerus.

5. The method of claim 1, wherein at least a portion of the exterior surface is convex, and the interior portion includes an interior surface, at least a portion of the interior surface being concave.

6. The method of claim 1, wherein the interior portion of said prosthesis includes a plurality of posts, wherein at least one of the plurality of posts includes an axially-extending aperture defined therein.

7. The method of claim 1, further comprising utilizing an extension portion extending outwardly from said prosthesis, inserting the extension portion in a medullary cavity of the humerus, and attaching the extension portion to the humerus.

8. The method of claim 6, further comprising inserting at least one fourth fastener through at least one fourth opening in the upper portion of said bone plate into the at least one axially-extending aperture defined in the at least one of the plurality of posts.

9. The method of claim 7, further comprising inserting at least one fourth fastener through at least one fourth opening in the elongated lower portion of said bone plate, through the shaft of the humerus, and into at least one opening defined in said extension portion.

10. A method for replacing at least a portion of a comminuted humeral head of a humerus, the method comprising:

utilizing a prosthesis having an exterior portion, the exterior portion having an exterior surface, and an interior portion, the interior portion having at least one first aperture and at least one second aperture formed therein, the exterior surface approximating the surface of at least a portion of the comminuted humeral head in size and shape;

utilizing a bone plate, said bone plate including an upper portion adapted to attach to the humerus at a position proximate a surgical neck thereof, and a lower portion adapted to attach to a shaft of the humerus;

removing at least a portion of the comminuted humeral head;

aligning at least one first opening in said upper portion of said bone plate with the at least one first aperture formed in the interior portion of said prosthesis, and aligning at least one second opening in said upper portion of said bone plate with the at least one second aperture formed in the interior portion of said prosthesis;

inserting at least one first fastener through the at least one first opening in said upper portion of said bone plate and into the at least one first aperture formed in the interior portion of said prosthesis, and inserting at least one second fastener through the at least one second opening in said upper portion of said bone plate and into the at least one second aperture formed in the interior portion of said prosthesis; and inserting at least one third fastener through at least one third opening defined in the lower portion of said bone plate and into the shaft of the humerus, thereby securing attachment of said prosthesis and said bone plate to one another and to the humerus, using the at least one first, second, and third fasteners.

11. The method of claim 10 further comprising utilizing an extension portion extending outwardly from the said prosthesis, and inserting said extension portion in a medullary cavity of the humerus.

12. The method of claim 11, further comprising inserting at least one fourth fastener through at least one fourth opening defined in the lower portion of said bone plate, through the shaft of the humerus and into at least one aperture defined in said extension portion.

* * * * *

UNITED STATES PATENT AND TRADEMARK OFFICE
CERTIFICATE OF CORRECTION

| | | |
|---|---|---|
| PATENT NO. | : 8,870,963 B2 | Page 1 of 1 |
| APPLICATION NO. | : 13/282810 | |
| DATED | : October 28, 2014 | |
| INVENTOR(S) | : Eduardo Gonzalez-Hernandez | |

It is certified that error appears in the above-identified patent and that said Letters Patent is hereby corrected as shown below:

<u>On Title Page 3, Item (56) References Cited, Other Publications</u>
Column 2, line 33, change "Plates (catalog)" to --Plate System (catalog)--;
Column 2, line 47, change "B.R. Braaksrna, G,B," to --Braaksma, G.B.--;
Column 2, line 67, change "Locking System;" The" to --Locking System," The--;
Column 2, line 69, change "Zimmer; Inc.;" to --Zimmer, Inc.--;
Column 2, line 71, change "Zimmer; Inc.;" to --Zimmer, Inc.--;

<u>On Title Page 4, Item (56) References Cited, Other Publications</u>
Column 1, line 5, change "Zimmer; Inc.;" to --Zimmer, Inc.--; and
Column 1, line 7, change "Zimmer Perlarticular Plating" to --Zimmer Periarticular Plating--.

Signed and Sealed this
Seventeenth Day of February, 2015

Michelle K. Lee
*Deputy Director of the United States Patent and Trademark Office*